(12) United States Patent
Stojanovic et al.

(10) Patent No.: US 11,957,644 B1
(45) Date of Patent: Apr. 16, 2024

(54) THERAPEUTIC PREPARATION OF ACTIVATED ST. JOHN'S WORT

(71) Applicants: Natasa Stojanovic, Irvine, CA (US); Robert D. Fish, Irvine, CA (US)

(72) Inventors: Natasa Stojanovic, Irvine, CA (US); Robert D. Fish, Irvine, CA (US)

( * ) Notice: Subject to any disclaimer, the term of this patent is extended or adjusted under 35 U.S.C. 154(b) by 0 days.

(21) Appl. No.: 17/960,817

(22) Filed: Oct. 5, 2022

(51) Int. Cl.
| | | |
|---|---|---|
| *A61K 31/122* | (2006.01) | |
| *A61K 36/18* | (2006.01) | |
| *A61K 41/10* | (2020.01) | |
| *A61K 47/26* | (2006.01) | |
| *A61K 47/44* | (2017.01) | |

(52) U.S. Cl.
CPC ........... *A61K 31/122* (2013.01); *A61K 36/18* (2013.01); *A61K 41/10* (2020.01); *A61K 47/26* (2013.01); *A61K 47/44* (2013.01); *A61K 2236/31* (2013.01); *A61K 2236/35* (2013.01)

(58) Field of Classification Search
CPC ...... A61K 31/122; A61K 36/18; A61K 41/10; A61K 47/26; A61K 47/44; A61K 2236/31; A61K 2236/35
See application file for complete search history.

(56) References Cited

U.S. PATENT DOCUMENTS

2004/0265395 A1* 12/2004 Sun ................... A61K 31/60
424/617

* cited by examiner

*Primary Examiner* — Robert A Wax
*Assistant Examiner* — Quanglong N Truong
(74) *Attorney, Agent, or Firm* — Fish IP Law, LLP

(57) ABSTRACT

A therapeutic composition and a method of producing it by light-activating hypericin in a carrier or solvent. Preferably, the composition is made by combining dried flowers and/or flower stems of St. John's Wort with edible oil and exposing the mixture to the sun for a prolonged time. This process serves to light-activate the hypericin before its use and reduce risk of skin phototoxicity. The composition can be used for treating undesirable conditions such as mouth sores and vaginal infections.

16 Claims, 2 Drawing Sheets

THERAPEUTIC PREPARATION OF ACTIVATED ST. JOHN'S WORT

FIELD OF THE INVENTION

The field of the invention is therapeutic preparations.

BACKGROUND

The following description includes information that may be useful in understanding the present invention. It is not an admission that any of the information provided herein is prior art or relevant to the presently claimed invention, or that any publication specifically or implicitly referenced is prior art.

St. John's Wort, or Kantarion *Hypericum perforatum*, is a plant in the family Hypericaceae that contains hypericin and has been used and studied for centuries for its medical benefits. Some of its observed benefits include anti-inflammatory, anti-viral and anti-cancer properties, and known uses include topical treatment for burns, abrasions and wounds. St. John's Wort is usually administered orally as a dietary supplement. Moreover, it has been observed that its beneficial effects are activated mostly when the hypericin is irradiated by a source of light. However, when a high concentration of hypericin becomes light-activated through the skin, it can induce skin phototoxicity, causing irritation and sensibility to the sun.

Thus, there is a need for both topically applying and orally ingesting hypericin containing compositions that avoid or at least reduce inflammation and other side effects, and especially compositions derived from the commonly used St. John's Wort, which ameliorate such side effects.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The recitation of ranges of values herein is merely intended to serve as a shorthand method of referring individually to each separate value falling within the range. Unless otherwise indicated herein, each individual value is incorporated into the specification as if it were individually recited herein, and ranges include their endpoints.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention. Unless a contrary meaning is explicitly stated, all ranges are inclusive of their endpoints, and open-ended ranges are to be interpreted as bounded on the open end by commercially feasible embodiments.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

SUMMARY OF THE INVENTION

It has now been surprisingly discovered that when hypericin is activated while disposed in a mixture with a suitable carrier or solvent, and then ingested or topically applied, the activated composition is effective with reduced side effects.

In preferred embodiments, the hypericin is derived from a flower and/or flower stem of a plant in the family Hypericaceae, and the carrier or solvent comprises an edible oil. The oil in this case acts as a carrier for both the flowers and/or flower stems, and as a solvent for the hypericin that is drawn out of the flowers and/or flower stems.

Irradiation can be accomplished in any suitable manner, including by sunlight.

In preferred embodiments, the therapeutic composition can be made by picking St. John's Wort's flowers and/or flower stems in the summer, when the flowers have the most yellow coloring, drying and cutting the flowers and/or flower stems, placing them in a jar or bottle with olive oil, and setting the mixture outside in the sun for several days or weeks. The drying process can be accomplished in any suitable manner, including by upending the flowers for two to three days.

Also in preferred embodiments, the mixture of St. John's Wort's flowers and/or flower stems and olive oil is light-activated by setting it outside in the sun for at least 20 days, with shaking and turning every day. A clarified oil is then prepared by removing at least most of the flowers and/or flower stems from the light-activated mixture.

Contemplated therapeutic compositions can be used to treat a variety of conditions, including for example hemorrhoids, varicose veins, vaginal infections, and mouth sores.

As used herein, the term "therapeutically-packaged" means packaged as intended for use on or in the body of a person for medical treatment.

As used herein, the term "mixture" means a combination of constituent components, whether solvated, blended, emulsified, decocted, or otherwise combined.

As used herein, the term "light-activated mixture" means a mixture that has been irradiated with a source of light following combining of its constituent components. A mixture of dried flowers and/or dried stems in oil or other carrier or solvent, which is then irradiated, is still considered to be a light-activated mixture even though one or more additional components are added after irradiation.

As used herein, the term "dry" or "dried" flowers and/or flower stems means flowers and/or flowers stems that have been reduced in water content by at least 25% wt/wt, more preferably by at least 50% wt/wt, still more preferably by at least 75% wt/wt, and most preferably by at least 90% wt/wt.

Various objects, features, aspects and advantages of the inventive subject matter will become more apparent from the following detailed description of preferred embodiments, along with the accompanying drawing figures in which like numerals represent like components.

DETAILED DESCRIPTION (OF THE DRAWING)

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

Figure 1:
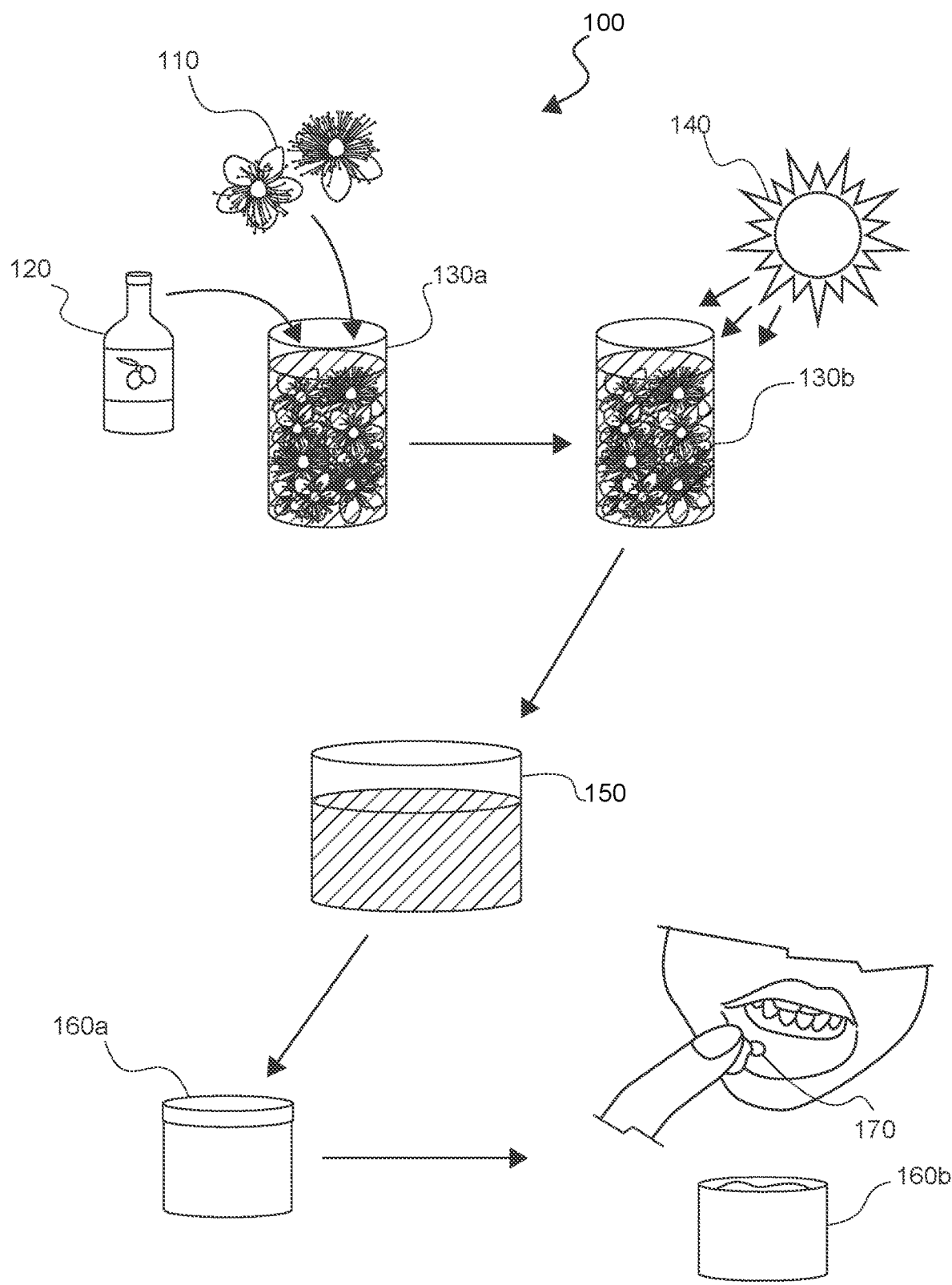
FIG. 1 is a graphic representation of the therapeutic composition in preferred embodiments according to the inventive subject matter, and of the method of using the therapeutic composition to treat undesirable conditions.

FIG. 1 generally depicts the preferred embodiment of the therapeutic composition where flowers of St. John's Wort (110), and olive oil (120) are provided. The flowers and the olive oil are then placed in a container (130) and exposed to sunlight (140) for a prolonged time. A clarified oil is then prepared by separating the flowers from the oil, resulting in a therapeutic composition (150). The composition is then therapeutically-packaged (160a), and lastly applied topically (160b) to treat a mouth sore (170).

Figure 2:
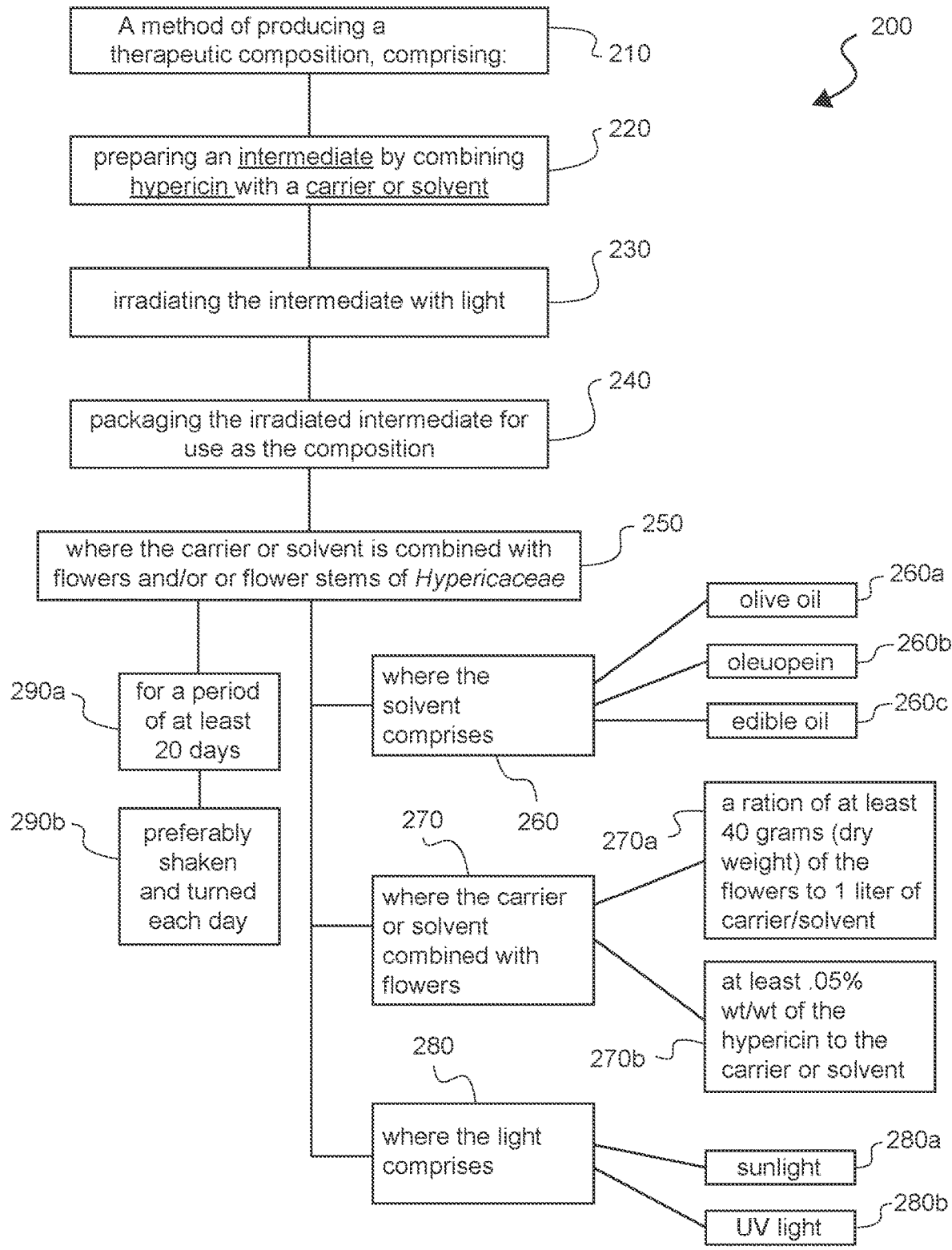
FIG. 2 is a flowchart of steps to prepare the therapeutic composition in preferred embodiments according to the inventive subject matter, including various alternatives.

In FIG. 2, schematic 200 depicts a method (210) of producing a therapeutic composition comprising three basic steps:

Step 220—preparing an intermediate by combining hypericin with a carrier or solvent;

Step 230—irradiating the intermediate with light; and

Step 240—packaging the irradiated intermediate for use as the composition.

The intermediate can be prepared by combining the carrier or solvent with at least one of flower and/or flower stem of a Hypericaceae plant (250). The carrier or solvent-immersed flowers and/or flower stems may comprise the following (270):

Box 270a—at least 1% wt/wt of a dry weight of the flowers and/or flower stems to the carrier or solvent. In preferred embodiments, the carrier or solvent-immersed flowers and/or flower stems comprise a ratio of at least 40 grams of a dry weight of the flowers and/or flower stems to one liter of the carrier or solvent.

Box 270b—additionally or alternatively hypericin can be added in some form other than in dried flowers or stems, and in that case hypericin is added to the carrier or solvent in a concentration of at least 0.05% wt/wt of the hypericin to the carrier or solvent.

Some contemplated options for the carrier or solvent are as follows (260):

Box 260a—olive oil.

Box 260 b—oleuropein.

Box 260c—edible oil.

Some contemplated options for the light are (280):

Box 280a—sunlight.

Box 280b—UV light.

The carrier or solvent can be combined with at least one of flowers and/or flower stems of a Hypericaceae plant and irradiated with light for at least 20 days (290a), preferably shaken and turned every day (290b).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of producing a therapeutic composition, comprising:

preparing an intermediate by combining hypericin with a carrier or solvent;

irradiating the intermediate with light; and then packaging the irradiated intermediate in a vial for ingestion or topical use as the therapeutic composition.

2. The method of claim 1, wherein the step of preparing the intermediate comprises combining the carrier or solvent with at least one of a flower and/or a flower stem of a plant in the family Hypericaceae.

3. The method of claim 2, wherein the carrier or solvent comprises an edible oil.

4. The method of claim 3, wherein the carrier or solvent comprises olive oil.

5. The method of claim 3, wherein the carrier or solvent comprises oleuropein.

6. The method of claim 3, wherein the carrier or solvent-immersed flowers and/or flower stems comprise a ratio of at least 40 grams of a dry weight of the flowers and/or flower stems to one liter of the carrier or solvent.

7. The method of claim 3, wherein the carrier or solvent-immersed flowers and/or flower stems comprise at least 0.05% wt/wt of the hypericin to the carrier or solvent.

8. The method of claim 2, wherein the light comprises sunlight.

9. The method of claim 2, wherein the light comprises ultraviolet light.

10. The method of claim 1, wherein the step of preparing the intermediate comprises combining the carrier or solvent with a flower and/or flower stem of a plant in the family Hypericaceae, the carrier or solvent comprises olive oil, and the light comprises sunlight, further comprising subjecting the intermediate to the sunlight for a period of at least 20 days, and further comprising shaking and turning the intermediate each day.

11. A method of treating a body of a person, comprising:
  providing in a container, a light-activated mixture of (a) a plant material comprising a dried flower and/or flower stem of a plant in the family Hypericaceae, and (b) an edible oil;
  preparing a clarified oil by removing at least some of the plant material from the light-activated mixture; and
  removing a portion of the clarified oil from the container, and applying the removed clarified oil to a region of the body having an undesirable condition.

12. The method of claim 11, wherein the undesirable condition comprises a hemorrhoid.

13. The method of claim 11, wherein the undesirable condition comprises a varicose vein.

14. The method of claim 11, wherein the undesirable condition comprises a vaginal infection.

15. The method of claim 11, wherein the undesirable condition comprises a mouth sore.

16. The method of claim 11, wherein the step of providing the clarified oil to a region of the body comprises ingesting a dose of the clarified oil.

\* \* \* \* \*